United States Patent [19]

Umezu et al.

[11] Patent Number: 4,906,794

[45] Date of Patent: Mar. 6, 1990

[54] LYSOSOME LIBERATION INHIBITORS AND HISTAMINE RELEASE INHIBITORS

[75] Inventors: Kohei Umezu, Yokohama; Koichiro Hirayama, Sagamihara; Kazuo Suzuki, Ami, all of Japan

[73] Assignee: Mitsubishi Kasei Corporation, Tokyo, Japan

[21] Appl. No.: 308,476

[22] Filed: Feb. 10, 1989

Related U.S. Application Data

[62] Division of Ser. No. 128,591, Dec. 1, 1987.

[30] Foreign Application Priority Data

Dec. 9, 1986 [JP] Japan .................................. 61-292747

[51] Int. Cl.$^4$ ...................... C07C 35/205; C07C 33/05
[52] U.S. Cl. ..................................... 568/821; 560/231; 560/249
[58] Field of Search ................. 568/821; 560/249, 231

[56] References Cited

U.S. PATENT DOCUMENTS 4,701,570 10/1987 Mizusaki et al. .................... 568/821

FOREIGN PATENT DOCUMENTS 39651 3/1977 Japan .................................. 568/821
22624 2/1980 Japan .................................. 560/249

OTHER PUBLICATIONS

Chem. Abst., 95:169547f, (1981), "Cembrane diterpenes from Sarcophyton Glaucun", Mitsubishi Chem. Ind.
Chem. Abst., 95:169548g, (1981), "Cembrane diterpenes", Mitsubishi Chem. Ind.
Chemical Abstract 92:73002m (1980).
Chemical Abstract 95:150962r (1981).
Chemical Abstract 95:169547f (1981).
Chemical Abstract 95:169548g (1981).

Primary Examiner—Werren B. Lone
Attorney, Agent, or Firm—Oblon, Spivak, McClelland, Maier & Neustadt

[57] ABSTRACT

The present invention provides lysosome liberation inhibitors comprising, as effective ingredients, cembrane-type diterpene compounds represented by the general formula (I) or (II):

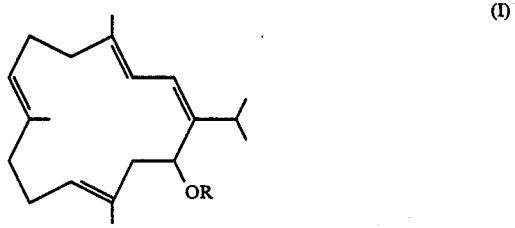

(I)

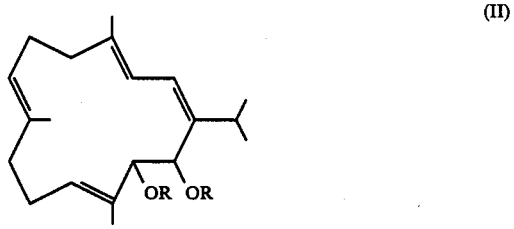

(II)

wherein R is a hydrogen atom or an acyl group.

Also provided is histamine release inhibitors comprising the cembrane-type diterpene compounds represented by the general formula (I) or (II) above as effective ingredients.

7 Claims, No Drawings

LYSOSOME LIBERATION INHIBITORS AND HISTAMINE RELEASE INHIBITORS

This is a division of application Ser. No. 07/128,591, filed Dec. 1, 1987.

BACKGROUND OF THE INVENTION

1. Field of the Invention

This invention relates to lysosome liberation inhibitors and histamine release inhibitors, which comprise certain cembrane-type diterpene compounds as active ingredients.

2. Description of the Prior Art

Cembrane-type diterpene compounds are found in coelenterates belonging to the orders Gorgonacea and Alcyonacea. Recently, some of them have been found to exhibit an anti-tumor activity: see, for instance, B. Tursch et al., Tetrahedron, 31, 129 (1975); and A. J. Weinheimer et al., Tetrahedron Letters, 2923 (1977).

Under these circumstances, Hirayama et al. have studied a coelenterate "Ohumikinoko" (Sarcophyton glaucum) belonging to the order Alcyonacea and finally discovered new cembrane-type diterpene compounds having an anti-solid tumor activity: see, for instance, Japanese Patent Application Laying-open (KOKAI) No. 61318/81.

Although such anti-solid tumor activities of these compounds have been reported, there has been no report on their anti-inflammatory activities or their effects on inflammatory cells such as polymorphonuclear leukocytes and mast cells.

Recently, it has been said that there may be some doubts in the prostaglandin hypothesis which has importantly been utilized to elucidate the etiology of chronic inflammation. Instead, a new, active oxygen hypothesis has been proposed. Thus, polymorphonuclear leukocytes and macrophages possess a phagocytic activity and are said to digest intruding foreign materials and to kill invading bacteria. Reactions of polymorphonuclear leukocytes or macrophages with bacteria or antigen-antibody complexes will produce active oxygen $O_2^-$ and/or hydroxyl radical OH, thereby directly causing damage to tissues and/or resulting in liberation of lysosomal enzymes.

There have been many reports suggesting a certain intimate relationship between inflammation and lysosomal enzymes liberated from leukocytes.

At present, chronic inflammation in which lysosomes may be involved may include rheumatoid arthritis, nephritis, pseudogout etc. In these diseases, pathological liberation of lysosomes will cause inflammatory conditions accompanied with pain. Thus, it is considered that chronic inflammation may be caused by persistent liberation of lysosomes into extracellular environment.

If such liberation of lysosomes could be inhibited, the conversion of inflammatory conditions into chronic ones would be delayed and/or prevented.

It has been known that mast cells are basophilic granulocytes which are widely found in various connective tissues and show metachromasia upon staining with basic dyes. It has also been known that the mast cells release mediators of allergic reactions such as histamine and leukotrienes.

Formerly, connective tissues were recognized merely as possessing supporting function. However, the connective tissues may now have been considered to control various cellular activities, e.g., cellular nourishment, elimination of cellular metabolites, preservation of cellular environment, protection of cell groups from extraneous invasion by serving as inflammatory sites, or the like.

In the course of the recent progress in cell biology and biochemistry, mast cells per se have become again recognized as very important cells responsible for a variety of physiological activities: "TAISHA" (Metabolism), Vol. 13, No. 5, "Special Issue on Mast Cells", Nakayama Shoten, Tokyo, Japan.

In recent years, for instance, new findings as to the etiology of ulcerative colitis have been accumulated and, as a result, destruction of the defense mechanism against invasion of antigens such as bacteria from the intestinal tract and establishment of autoimmunity to the colic mucosa are now considered to be the pathogenesis of persistent inflammation in the colic mucosa, which is a main symptom of this disease.

Both immediate-type and delayed-type allergies are involved in this ulcerative colitis. In its acute stage, the establishment of the immediate-type allergy in the colic mucosa will cause the symptoms. Thus, elevated plasma histamine levels, increases of eosinophils in the colic mucosa, and decreases of mast cells may be observed at this stage. The immediate-type allergy will cause induction of vasoactive substances and disturbance of intestinal microcirculation and, correspondingly, various acute sumptoms are developed due to hyperpermeability of the intestinal mucosa and enhanced myospasm.

It has been reported that cromoglycate, which inhibits degranulation of mast cells, namely, which is an inhibitor of histamine release, may be effective in the ulcerative colitis. Thus, compounds having a potent inhibitory activity against release of histamine from mast cells may be expected to be very effective for the treatment of ulcerative colitis.

It has recently become recognized that histamine plays an important role not only as a mediator of the initial stage in acute inflammation but also as an agent controlling conversion of inflammation into chronic conditions as well. For instance, it is said that histamine receptors are present in fibroblasts and collagen production in the cells is enhanced by histamine. In addition, the fact that mast cells will increase in fibrous tissues with inflammation has been established.

Accordingly, inhibition of histamine release from mast cells would suppress, in an indirect manner, acceleration of fibrosis, i.e., enhancement of collagen production, in tissues under chronic inflammatory conditions. For example, such inhibition may be useful in the treatment of diseases accompanied with abnormal fibrous proliferation, pulmonary fibrosis, postoperative cheloids, abnormal fibrous proliferation due to trauma.

SUMMARY OF THE INVENTION

The present inventors have studied for the purpose of finding active substances having lysosome liberation and histamine release inhibitory activities. In the course of the studies, the present inventors paid their attentions to the effect of cembrane-type diterpene compounds contained in coelenterate Sarcophyton glaucum on the skin and have made great efforts to further develop such compounds. The present inventors have finally found that certain cembrane-type diterpene compounds may exhibit potent inhibitory activities against the liberation of lysosomes and the release of histamine. Thus, the present invention has been attained.

DESCRIPTION OF THE INVENTION

The present invention provides lysosome liberation inhibitors comprising as effective ingredients cembrane-type diterpene compounds represented by the following general formula (I) or (II):

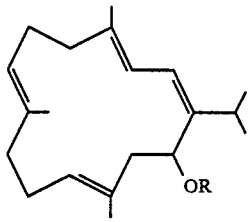
(I)

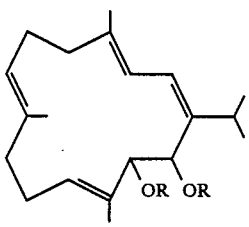
(II)

wherein R is a hydrogen atom or an acyl group.

The invention also provides histamine release inhibitors comprising the above described cembrane-type diterpene compounds as effective ingredients.

This invention will hereinafter be described in detail.

The cembrane-type diterpene compounds used in the invention are represented by the general formula (I) or (II) shown above.

In these formulae, R represents a hydrogen atom or an acyl group. Preferably, the acyl groups include acetyl, propionyl, butyryl and benzoyl groups.

These cembrane-type diterpene compounds may be prepared by known methods described in e.g. Japanese Patent Application Laying-open (KOKAI) Nos. 61317/81 and 61318/81, both of which are herein incorporated by reference.

Briefly, the compounds according to the invention may be separated from a lipid fraction of an extract from a soft coral "Ohumikinoko" (*Sarcophyton glaucum*) belonging to the order Alcyonacea by column chromatography on silica gel.

*Sarcophyton glaucum* generally lives on coral reefs in the Indian Ocean and the Pacific Ocean. For example, it has been known that *Sarcophyton glaucum* living in the Red Sea contains sarcophine and 16-deoxosarcophine see J. Bernstein et al., *Tetrahedron*, 30, 2817 (1974); and Y. Kashman et al., *Tetrahedron*, 30, 3615 (1974).

Substances contained in *Sarcophyton glaucum* extracts may vary depending on the seasons when and the places where samples of the coelenterate are collected. The seasons and places should suitably be chosen.

It is preferred that samples of the coelenterate *Sarcophyton glaucum* are dried and sliced into small pieces so as to eliminate the viscosity of the surface before extraction.

Solvents which can be used in the extraction may include such organic solvents as, for example, alcohols, such as methanol, ethanol, isopropanol, etc.; halogenated hydrocarbons, such as chloroform, etc.; hydrocarbons, such as benzene, hexane, heptane, etc.; ethers, such as ethyl ether, isopropyl ether, dioxane, etc.; ketones, such as acetone, methyl ethyl ketone, etc.; esters, such as ethyl acetate, etc.; and the like, as well as mixtures thereof.

To avoid oxidative degradation of the active substances contained in the extract, the extracting operation is preferably carried out either under those conditions where the area of portions to be contacted with air should be as small as possible, or under inert gas atmosphere.

The extraction may be preformed at room temperatures, but may also be carried out under heating so as to accelerate the extraction.

The liquid extract obtained by separation from residues in any conventional manner may be distilled by usual procedures to remove the remaining solvent. Thus, a crude product is obtained.

The crude product may be subjected to treatment with active charcoal or to fractionation by any usual method as described by J. Folch et al., in *J. Biol. Chem.*, 226, 497 (1957) to obtain a lipid fraction.

The thus obtained lipid fraction of the extract from *Sarcophyton glaucum* is a viscous, brown oil.

Such a lipid fraction can be further purified by chromatography. Column chromatography or preparative thin layer chromatography may be employed.

Packing materials which can be used in columns for chromatography may include silica gel, alumina, cellulose powder, active carbon, etc. Solvents used as eluents may be suitably chosen depending on the packing material employed. When silica gel is used as a packing material, hexane, or hexane/ethyl acetate with volume ratio of 0.95–0.9:0.05–0.1, is preferred.

Fractions in the chromatographic operation can be still further purified and/or isolated by column chromatography using other different packing materials and eluent solvents.

Gels which can be employed in the preparative thin layer chromatography may include silica gel, alumina, cellulose powder, etc. Solvents which may preferably be employed to develop include hexane-ethyl acetate as described above.

Among the thus obtained compounds represented by the general formula (I), one in which R is a hydrogen atom has been called sarcophytol-A.

This sarcophytol-A may be acylated in a conventional manner to give acylated derivatives such as sarcophytol-A acetate. Such acylated derivatives of sarcophytol-A can be in turn hydrolyzed by conventional methods to obtain sarcophytol-A.

On the other hand, among those compounds which may be obtained in a similar manner and represented by the general formula (II), one in which R is a hydrogen atom has been called sarcophytol-B.

This sarcophytol-B may also be acylated in a conventional manner to give acylated derivatives such as sarcophytol-B diacetate. Such acylated derivatives of sarcophytol-B can be in turn hydrolyzed by conventional methods to obtain sarcophytol-B.

It is not necessary that the thus isolated, pure cembrane-type diterpene compound represented by the general formula (I) or (II) should be employed as an active ingredient in the present inhibitor. It should be understood that any mixture of such pure compounds or any crude extract or partially purified product containing at least one of them can be used as active ingredients of the inhibitors according to the invention.

Thus, either at least one cembrane-type diterpene compound as obtained in the aforementioned method or any extract from *Ssaracophyton glaucum* or partially purified product containing such a compound is incorporated into the drug according to the present invention as an effective ingredient.

The lysosome liberation or histamine release inhibitors according to the invention may be administered in any way.

Parenteral administration routes such as subcutaneous, intravenous, intramuscular or intraperitoneal injections, as well as oral administration route may be possible.

Dose amounts of the present inhibitors will be suitably determined according to ages, conditions and body weights of patients to be treated, types and frequencies of concomitant therapy, and the therapeutic effect to be desired. In general, dose amounts of the effective ingredients may be in the range from 50 to 2,000 mg per day, particularly from 100 to 500 mg per day. These inhibitors may be administered, preferably orally, in a single dose or several doses per day.

For oral administration, the inhibitors of the invention may be used in the form of tablets, capsules, powders, elixirs, etc. For parenteral routes, they may be sterilized solutions or suspensions. These dosage forms of drugs may also contain one or more pharmaceutically acceptable, non-toxic, solid or liquid carriers or vehicles.

Examples of solid carriers may include conventional geletine capsules. One or more active ingredients can be tabletted, granulated or pulverized with or without one or more adjuvants, and they can then be packaged. These capsules, tablets and powders may generally contain 5 to 95% by weight, preferably 25 to 90% by weight, of the active ingredient(s).

Liquid carriers may include animal- or plant-derived oils such as peanut oil, soybean oil, mineral oil, sesame oil etc., and synthetic oils. Generally, preferred liquid carriers are saline; sugar solutions such as dextrose; glycols such as ethylene glycol, propylene glycol, polyethylene glycol and the like.

When the inhibitors of the invention are to be administered parenterally, i.e., by intramuscular, intravenous or subcutaneous injections, they may be employed in the form of sterilized solutions to which sodium chloride or other solute such as glucose has been added so as to make the solutions isotonic.

Solvents suitable for use in injections may include sterilized water, lidocaine hydrochloride solution for intramuscular injections, saline, glucose, intravenously injectable liquids, electrolyte solutions for intravenous injections, and the like. These injections may usually contain 0.5 to 20% by weight, preferably 1 to 10% by weight, of the active ingredient(s).

Liquid drugs for oral administration according to the invention may preferably be suspensions or syrups containing 0.5 to 10% by weight of the effective ingredient(s). The carriers contained in such liquid drugs may be water-like vehicles such as perfumes, syrups, pharmaceutical micelles, and the like.

The lysosome liberation inhibitors of the present invention are specific to inflammatory cells and exert little or no effect on such blood cells as erythrocytes and platelets.

Thus, the inhibitors of the invention, which have a strong affinity for inflammatory cells, will enter and dissolve into lipids within the cell membrane and inhibit the reactions of the cell inflammatory cells against external stimuli, so that the conversion of inflammation into chronic state due to aggravation or persistent status of the inflammation resulting from the destruction of inflammatory tissues by lysosomal enzymes may be suppressed.

The drugs of the invention can be administered orally and may potentially be effective for rheumatoid arthritis, osteoarthritis, pseudogout, and many other chronic inflammation The histamine release inhibitors of the invention have an active effect on mast cells and positively inhibit the release of histamine. Accordingly, these drugs may be effective for a variety of diseases induced by histamine. Thus, they are not only useful as antiallergic agents but also they are effective for other diseases whose pharmacological mechnism has recently been analyzed and in which mast cells may be considered to be etiologically involved, for example, ulcerative colitis.

DESCRIPTION OF THE PREFERRED EMBODIMENTS

The invention will hereinbelow be illustrated in more detail by the following examples. This invention should not be limited to these examples unless departing from the scope of the invention.

EXAMPLE 1

When 0.75 ml of 1% (W/V) λ-carrageenin is subcutaneously injected into the left paw of a Wistar male rat of 120 to 150 g, edema is developed in the left paw with a severity peak at 3 to 4 hours after injection—rat carrageenin edema test. It has been known that this carrageenin-induced rat paw edema is an excellent experimental model for inflammation, where histamine is involved in the development of edema immediately after injection of carrageenin, and subsequently such chemical mediators as prostaglandins, leukotrienes, bradykinin and the like are also involved.

The effect of sarcophytol-A on edema was investigated employing this experimental model: sarcophytol-A was orally administered to rats one hour before injection of carrageenin and the volume of the thus induced edema in the rat paw was measured by a volumometer 2 or 3 hours after the injection of carrageenin.

Degrees of edematization are expressed in percentages of paw volume increases after induction with respect to the paw volumes before induction: namely, $$\% \text{ Edematization} = (B-A)/A \times 100$$

wherein A is the paw volume before induction, and B after induction. Further, inhibiting rates (%) are calculated according to the following equation:

$$\% \text{ Inhibition} = (1-T/C) \times 100$$

wherein T is % edematization of the treated group, and C of the control group which was not treated with sarcophytol-A. The results are shown in Table 1.

TABLE 1

| Drug | Dose (mg/kg) | Number of Rats | % Inhibition 2 Hours | % Inhibition 3 Hours |
|---|---|---|---|---|
| Indomethacin | 10 | 6 | 43.5 ± 3.5** | 43.7 ± 3.0*** |
| Sarcophytol-A | 33 | 6 | −3.0 ± 6.5 | 2.4 ± 8.6 |
| Sarcophytol-A | 100 | 6 | 24.4 ± 7.8 | 26.9 ± 6.9** | p <0.01, *p <0.001, with respect to the control group.

EXAMPLE 2

When 20 ml of 1% casein is intraperitoneally injected to a rat, a large number of polymorphonuclear leukocytes appear in the peritoneal cavity in 5 hours after the injection. Using these polymorphonuclear leukocytes, it is possible to measure the activity of polymorphonuclear leukocytes in an in vitro system. Thus, polymorphonuclear leukocytes are added into a test tube together with a buffer, and cytochalasin B is then added. Five minutes later, a stimulant formyl-methionyl-leucyl-phenylalanine (FMLP) is added. Then, the polymorphonuclear leukocytes liberate lysosomal enzymes. Simultaneously, some active enzymes and leukotrienes are produced. See Wei Hsueh et al., Nature, 290(23), 710-713 (11981).

Using this experimental system, when the polymorphonuclear leukocytes were preincubated in the presence of sarcophytol-A before addition of the stimulant, the liberation of lysosomal enzymes were positively inhibited.

Thus, polymorphonuclear leukocytes ($2 \times 10^6$) were collected from the peritoneal cavity of a male Wistar rat of 250 to 350 g in body weight which had been stimulated with casein, and incubated in Hepes buffer (pH 7.4) for 5 minutes. After 5 μg of cytochalasin B was added, the mixture was incubated for an additional one minute. To the mixture, there was added an amount of a drug to be tested and, after incubation for 5 minutes, FMLP (0.1 μM) as a stimulant was added. Five minutes later, 2 volumes of ice-cooled phosphate buffer was added to arrest the reaction. The cells were removed by centrifugation at 1,100 rpm for 5 minutes. The supernatant was assayed for β-glucuronidase activity as an index of lysosomal enzymes. Separately, the total β-glucuronidase activity contained in the polymorphonuclear leukocyte was measured. Thus, liberation rates of lysosomal enzymes were determined as percentages of indices of the treated group to those of the control group. Inhibition rates were calculated in percentage according to the following equation:

% Inhibition = $(1 - T/C) \times 100$ wherein T and C represent the liberation rates (%) of lysosomes for the treated and control groups, respectively.

The results are shown in Table 2.

TABLE 2

| Drug | Concentration (μM) | Liberation (%) | Inhibition (%) |
|---|---|---|---|
| Control (0.1% DMSO) | | 32.0 | 0.0 |
| Sarcophytol-A | 4 | 29.4 | 8.1 |
| | 11 | 27.2 | 15.1 |
| | 33 | 26.0 | 18.8 |
| | 100 | 13.1 | 59.0 |

EXAMPLE 3

The release of histamine from mast cells can be demonstrated in vitro by employing mast cells prepared from rat peritoneal cavity: histamine can be released from mast cells when mast cells are incubated in the presence of an IgE antibody, e.g., one made in rabbits sensitized with a protein prepared from the cuticle of ascarids, followed by addition of an IgE antigen, e.g., a protein prepared from the cuticle of ascarids. Such histamine release can also be caused by addition of a synthetic stimulant compound 48/80, ATP (adenosine triphosphate), to mast cells.

Investigation using the stimulant compound 48/80 and the protein extracted from the cuticle of ascarids revealed that when mast cells were preincubated in the presence of sarcophytol-A before addition of the stimulant, the release of histamine was positively inhibited.

Thus, mast cells were collected from the peritoneal cavity of a male Wistar rat of 400 to 450 g in body weight according to conventional procedures. The mast cells ($5 \times 10^4$) were incubated in Krebs-Ringer buffer (pH 7.4) containing an amount of sarcophytol-A for 10 minutes. The compound 48/80 (100 ng) was added as a stimulant. After incubation for further 10 minutes, cells were removed by centrifugation. Histamine in the supernatant was quantitatively measured according to Shore et al. method: J. Phar. Exp. Ther., 127, 182-186 (1959). Total histamine contained in the mast cells was also measured. Inhibition rates (%) are calculated according to the following equation:

% Inhibition = $(T/C) \times 100$ wherein T and C represent the amount of histamine released from mast cells after the treatment with the drug, and the total amount contained in the mast cells, respectively.

TABLE 3:

| Drug | Concentration (μM) | Histamine Release* | Inhibition (%) |
|---|---|---|---|
| Control (0.1% DMSO) | | 62.42 | 0 |
| Sarcophytol-A | 4 | 65.32 | -4.6 |
| | 11 | 59.72 | 4.3 |
| | 33 | 55.72 | 10.7 |
| | 100 | 41.45 | 33.6 |

*Fluorescence Intensity.

What is claimed is:

1. A method for inhibiting lysosome liberation, which comprises administering to a patient in need thereof an effective amount of a cembrane-type diterpene compound represented by the general formula (I) or (II):

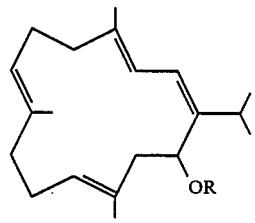

(I)

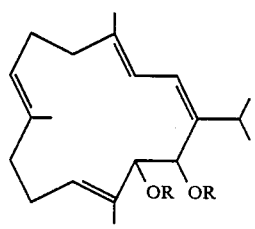

(II)

wherein R is a hydrogen atom or an acyl group.

2. The method in accordance with claim 1, in which the compound is sarcophytol-A represented by the formula (I) wherein R is hydrogen.

3. A method for inhibiting histamine release, which comprises adminstering to a patient in need thereof an effective amount of a cembrane-type diterpene compound represented by the general formula (I) or (II):

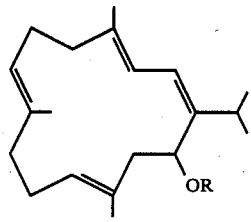
(I)

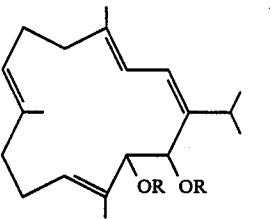
(II)

wherein R is a hydrogen atom or an acyl group.

4. The method in accordance with claim 1, in which the compound is sarcophytol-A represented by the formula (I) wherein R is hydrogen.

5. The method in accordance with claim 1 or 3, wherein said acyl group is selected from the group consisting of acetyl, propionyl, butyryl, and benzoyl.

6. The method of claim 1 or 3, wherein said patient is suffering from chronic inflammation.

7. The method of claims 1 or 3, wherein said effective amount ranges from 50 to 2,000 mg per day.

* * * * *